United States Patent
Hong et al.

[11] Patent Number: 5,990,311
[45] Date of Patent: Nov. 23, 1999

[54] PROCESS FOR PREPARATION OF PYRIMIDINE DERIVATIVES

[75] Inventors: You Wha Hong; Young Nam Lee; Hong Bae Kim, all of Kyonssi-do, Rep. of Korea

[73] Assignee: Uhan Corporation, Tongjiak-Ku, Rep. of Korea

[21] Appl. No.: 09/171,579

[22] PCT Filed: Apr. 30, 1997

[86] PCT No.: PCT/KR97/00073

§ 371 Date: Oct. 21, 1998

§ 102(e) Date: Oct. 21, 1998

[87] PCT Pub. No.: WO97/42186

PCT Pub. Date: Nov. 13, 1997

[30] Foreign Application Priority Data

| May 4, 1996 | [KR] | Rep. of Korea | 96-14538 |
| May 4, 1996 | [KR] | Rep. of Korea | 96-14539 |
| Oct. 29, 1996 | [KR] | Rep. of Korea | 96-49380 |
| Oct. 29, 1996 | [KR] | Rep. of Korea | 96-49381 |
| Oct. 29, 1996 | [KR] | Rep. of Korea | 96-49382 |

[51] Int. Cl.$^6$ .................................................. C07D 239/48
[52] U.S. Cl. ............................................. 544/324; 544/323
[58] Field of Search ................................. 544/331, 323, 544/324

[56] References Cited

U.S. PATENT DOCUMENTS 5,750,531  5/1998  Lee et al. ................................. 514/256

FOREIGN PATENT DOCUMENTS

| 0230871 | 8/1987 | European Pat. Off. |
| 0337943 | 10/1989 | European Pat. Off. |
| 0560726 | 9/1993 | European Pat. Off. |
| 9118887 | 12/1991 | WIPO |
| 9414795 | 7/1994 | WIPO |
| 9605177 | 2/1996 | WIPO |

OTHER PUBLICATIONS

Chemical Abstracts, vol. 96, Apr. 12, 1982, p. 697, col. 1, abstract No. 122741v, "Herbicides . . .".
Chemical Abstracts, vol. 118, Jun. 21, 1993, p. 347, col. 2, abstract No. 249869w, "Biosynthesis . . .".
Chemical Abstracts, vol. 106, Feb. 2, 1987, p. 526, col. 1, abstract No. 32801k, "Carbon dioxide . . .".
Chemical Abstracts, vol. 96, Jun. 21, 1982, p. 726, col. 1, abstract No. 217665n, "Synthesis . . .".

*Primary Examiner*—John M. Ford
*Attorney, Agent, or Firm*—Ladas & Parry

[57] ABSTRACT

The present invention relates to a process for preparation of 5,6-dimethyl-2-(4-fluorophenyl-amino)-4-(1-methyl-1,2,3,4-tetrahydroisoquinolin-2-yl)pyrimidine represented by the following formula (I),

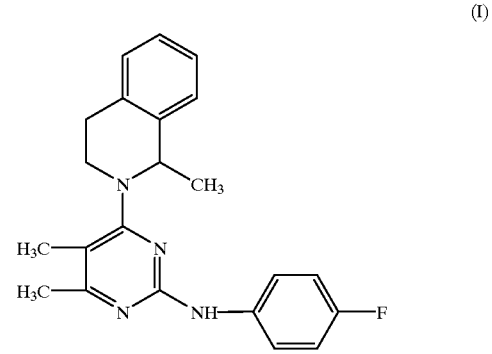

(I)

and its acid addition salts by reacting a pyrimidine derivative represented by the formula (II-A),

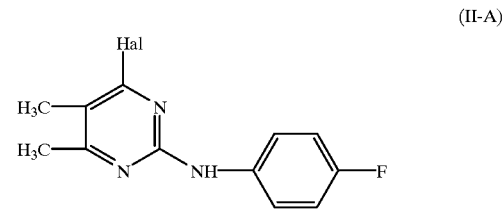

(II-A)

in which Hal represents a halogen, with 1-methyl-1,2,3,4-tetrahydroisoquinoline represented by the formula (III),

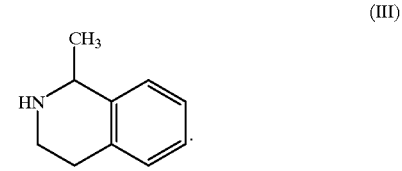

(III)

8 Claims, No Drawings

PROCESS FOR PREPARATION OF PYRIMIDINE DERIVATIVES

TECHNICAL FIELD

The present invention relates, first, to a process for preparation of 5,6-dimethyl-2-(4-fluorophenylamino)-4-(1-methyl-1,2,3,4-tetrahydroisoquinolin-2-yl)pyrimidine represented by the following formula (I) and its acid addition salts; second, to a process for preparation of an intermediate for preparing the compound (I); and, third, to a novel intermediate compound. More specifically, the present invention relates, first, to a process for preparation of 5,6-dimethyl-2-(4-fluorophenylamino)-4-(1-methyl-1,2,3,4-tetrahydroisoquinolin-2-yl)pyrimidine represented by the following formula (I),

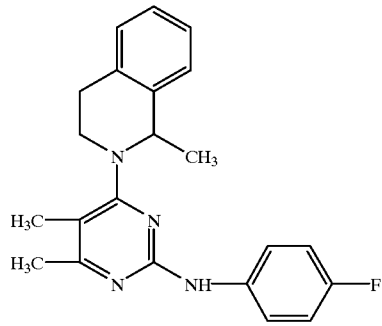

(I)

and its acid addition salts, wherein a pyrimidine derivative represented by the following formula (II-A),

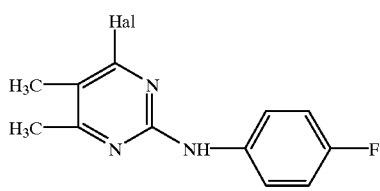

(II-A)

in which Hal represents a halogen, is reacted with 1-methyl-1,2,3,4-tetrahydroisoquinoline represented by the following formula (III);

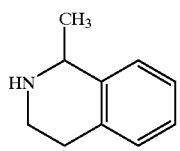

(II)

second, to a process for preparation of the pyrimidine derivative represented by formula (II-A) and the compound of formula (III); and, third, to a novel intermediate compound including the pyrimidine derivative represented by formula (II-A).

BACKGROUND ART 5,6-Dimethyl-2-(4-fluorophenylamino)-4-(1-methyl-1,2,3,4-tetrahydroisoquinolin-2-yl)pyrimidine of the above formula (I) inhibits gastric acid secretion by means of a reversible proton-pump inhibiting effect and, therefore, can be used as an anti-ulcer agent. This compound was developed by the inventors of the present invention, who then applied for patents for the compound and/or its method of preparation in Korea and other countries (see International Publication No. WO 96/05177).

According to the method disclosed in the above patent application, 5,6-dimethyl-2-(4-fluorophenylamino)-4-(1-methyl-1,2,3,4-tetrahydroisoquinolin-2-yl)pyrimidine is prepared according to the following reaction scheme A:

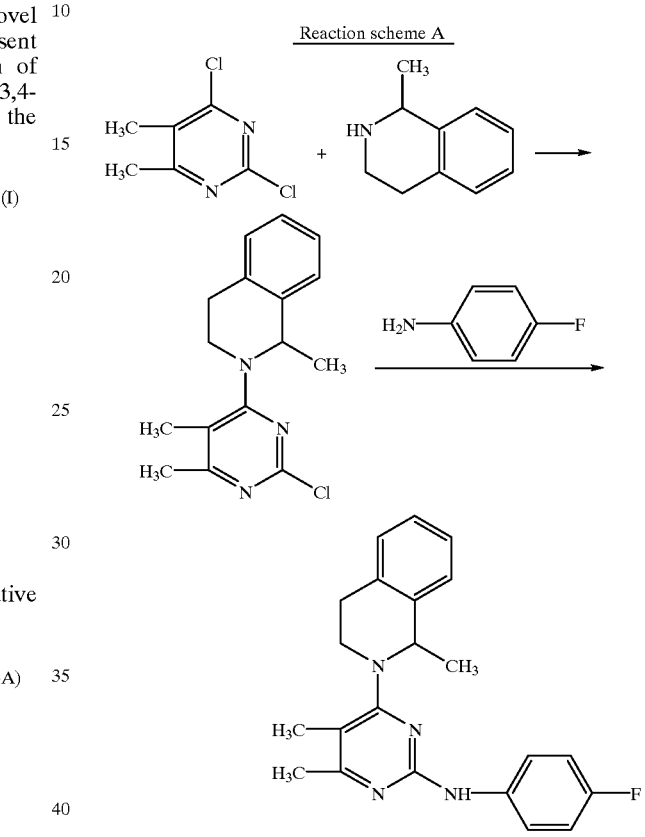

Reaction scheme A

Since the starting material of the above reaction scheme has two reactive sites (i.e., the two Cl atoms), the first reaction inevitably produces a side product, which reduces the yield of the desired compound.

The present inventors have long labored to develop a novel method for preparing 5,6-dimethyl-2-(4-fluorophenylamino)-4-(1-methyl-1,2,3,4-tetrahydroisoquinolin-2-yl)pyrimidine of formula (I) without producing side products. As a result, we have discovered that the desired compound of formula (I) can be efficiently prepared without side products by reacting the pyrimidine derivative represented by formula (II-A) with 1-methyl-1,2,3,4-tetrahydroisoquinoline represented by formula (III) and, thus, have completed the present invention.

DISCLOSURE OF THE INVENTION

The present invention relates to a novel process for preparation of 5,6-dimethyl-2-(4-fluorophenylamino)-4-(1-methyl-1,2,3,4-tetrahydroisoquinolin-2-yl)pyrimidine represented by formula (I) and its acid addition salts.

More specifically, the present invention relates to a process for preparation of 5,6-dimethyl-2-(4-fluorophenylamino)-4-(1-methyl-1,2,3,4-tetrahydroisoquinolin-2-yl)pyrimidine represented by formula (I),

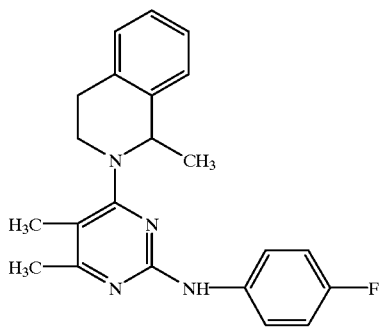

and its acid addition salts wherein a pyrimidine derivative represented by the following formula (II-A),

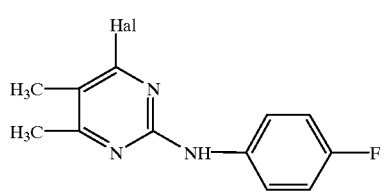

in which Hal represents a halogen, is reacted with 1-methyl-1,2,3,4-tetrahydroisoquinoline represented by formula (III),

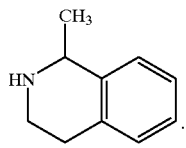

In addition, the present invention relates to a process for preparation of the pyrimidine derivative of formula (II-A) and the compound of formula (III).

Further, the present invention relates to a novel intermediate compound represented by the following formula (II), which includes the pyrimidine derivative represented by formula (II-A),

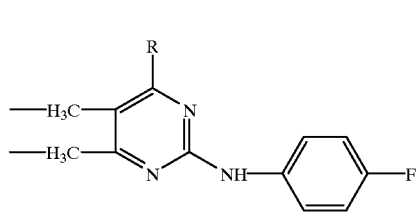

in which R represents hydroxy or a halogen.

BEST MODE FOR CARRYING OUT THE INVENTION

According to the present invention, the compound of formula (I) can be prepared by reacting the compound of formula (II-A) with 1-methyl-1,2,3,4-tetrahydroisoquinoline of formula (III), as depicted in the following reaction scheme 1:

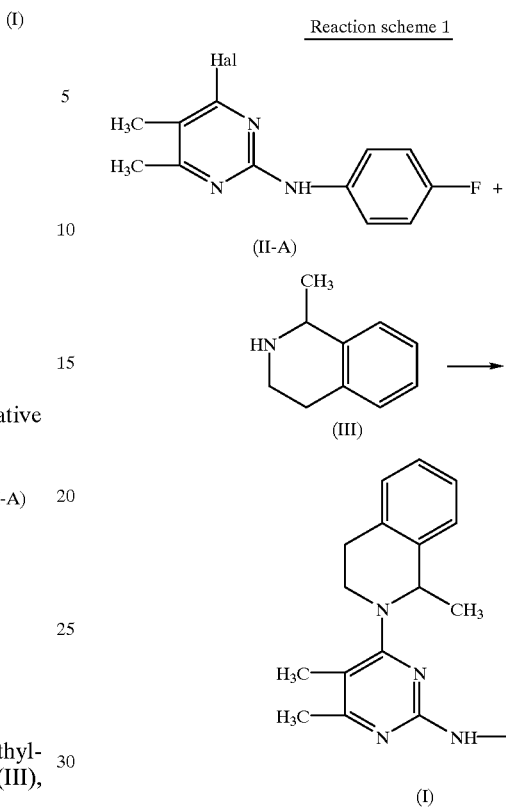

Since the starting compound of the reaction scheme 1 (i.e., the compound of formula (II-A)) contains a single reactive site (i.e., Hal), this reaction scheme does not produce any side product and, thus, optimizes the yield of the compound of formula (I), the desired product.

The present invention is described in more detail below.

Although the 4-halogeno-2-(4-fluorophenylamino)-5,6-dimethylpyrimidine represented by formula (II-A) can be reacted according to the present invention with an equivalent amount of 1-methyl-1,2,3,4-tetrahydroisoquinoline represented by formula (III), it is preferable to conduct the reaction using an excess, rather than an equivalent amount, of the latter. Since the latter is a liquid under reaction conditions, the unreacted 1-methyl-1,2,3,4-tetrahydroisoquinoline can be readily removed after the reaction has gone to completion.

The reaction of the present invention is preferably carried out in the presence of a solvent. Solvents which may be used for this purpose include N,N-dimethylformamide, n-butanol, n-pentanol, n-hexanol, dimethylsulfoxide, ethylene glycol, 1,2-propylene glycol, and mixtures thereof. Of these propylene glycol and ethylene glycol are most preferred, since use of either of these minimizes both reaction time and production of side products.

In the method of the present invention, the reaction scheme 1 is generally carried out in the presence of a base. Bases which can be used for this purpose include triethylamine, N,N-dimethylaniline, pyridine and potassium acetate. The reaction temperature for the reaction between the compound of formula (II-A) and 1-methyl-1,2,3,4-tetrahydroisoquinoline of formula (III) is preferably in the range from 110° C. to 160° C. and the reaction time is preferably in the range from 16 hours to 72 hours.

5,6-Dimethyl-2-(4-fluorophenylamino)-4-(1-methyl-1,2,3,4-tetrahydroisoquinolin-2-yl)pyrimidine of formula (I) as prepared according to the above method can be converted into its acid addition salt, preferably into the hydrochloride salt, by conventional methods. The resulting product can be purified by conventional working-up procedures, such as recrystallization, chromatography, and the like.

Since the compound of formula (I) prepared by the method of the present invention contains an asymmetric carbon atom (i.e., the carbon atom denoted by * in the formula immediately below), this compound be present in an (R)-(+)-isomer, an (S)-(−)-isomer, or a racemate wherein the R and S isomers are mixed in the ratio of 1:1. Unless indicated otherwise, the compound of formula (I) should be interpreted to include all of these isomers.

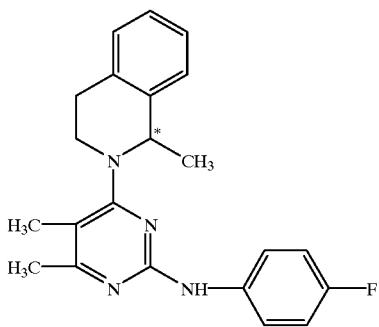

The (R)-(+)- and (S)-(−)-isomers of the compound of formula (I) can be readily be prepared from the R and S isomers, respectively, of the compound of formula (III).

The compound of formula (II-A), which is used as the starting material in the method of the present invention, is a novel compound which can be prepared according to the method depicted by the following reaction scheme 2:

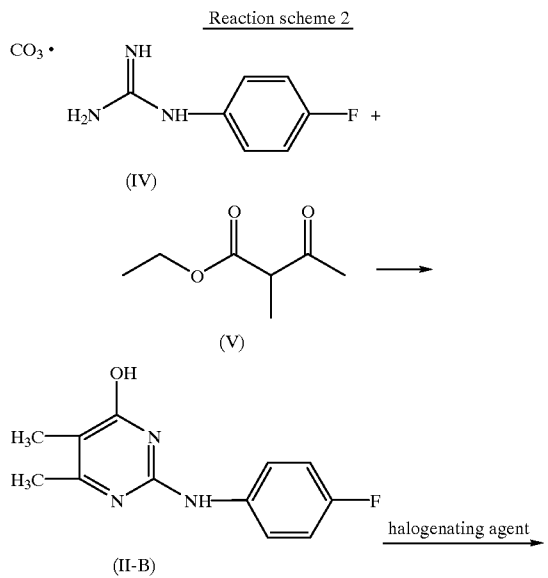

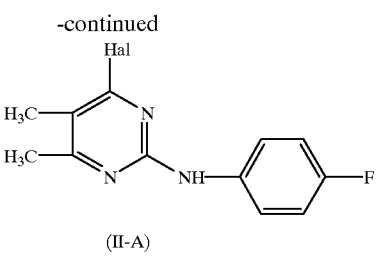

(II-A)

In the reaction scheme 2, Hal represents a halogen.

As depicted by the reaction scheme 2, reacting 4-fluorophenylguanidine carbonate of formula (IV) with ethyl 2-methylacetoacetate of formula (V) yields 4-hydroxy-2-(4-fluorophenylamino)-5,6-dimethylpyrimidine of formula (II-B), which may then be reacted with a halogenating agent to obtain the 4-halogeno-2-(4-fluorophenylamino)-5,6-dimethylpyrimidine of formula (II-A).

4-Fluorophenylguanidine carbonate of formula (IV), which is used as the starting material for preparing the compound of formula (II-A) in the reaction scheme 2, can readily be prepared from 4-fluoroaniline using known methods (see, for example, European Patent No. 0,560,726). Specifically, the desired 4-fluorophenylguanidine carbonate can be prepared by reacting 4-fluoroaniline with a 50% cyanamide solution under acidic conditions using 30% to 37% hydrochloric acid while maintaining the temperature ranging from 75° C. to 95° C.

The first step of the reaction scheme 2 may be practiced in the presence of a solvent. Solvents which may be used for this purpose include acetonitrile, N,N-dimethylformamide and dimethylsulfoxide. This reaction is preferably carried out at a temperature ranging from 110° C. to 160° C.

In the second step of the reaction scheme 2, 4-hydroxy-2-(4-fluorophenylamino)-5,6-dimethylpyrimidine of formula (II-B) obtained from the first step of the reaction scheme 2 is converted into the compound of formula (II-A) by reacting the former with a halogenating agent. Halogenating agents which can be used for this purpose include phosphorus oxychloride, oxalyl chloride, thionyl chloride and phosphorus tribromide. This halogenation reaction is carried out in the presence of a solvent. Reaction solvents which can be used for this purpose include preferably N,N-dimethylformamide, dimethylsulfoxide, 1,2-dichloroethane and 1,2-dichlorobenzene. It is preferable to maintain the reaction temperature in the range from 75° C. to 95° C.

Although the second step of the reaction scheme 2 can be practiced by isolating the intermediate after the first reaction step has been completed, it is preferable to conduct the first and second steps in a single vessel. Specifically, 4-hydroxy-2-(4-fluorophenylamino)-5,6-dimethylpyrimidine of formula (II-B) is prepared from 4-fluorophenylguanidine cabonate and then, without isolation, can be successively reacted with the halogenating agent to yield 4-halogeno-2-(4-fluorophenylamino)-5,6-dimethylpyrimidine (II-A).

The compound of formula (II-A), which is used as the starting material for preparation of the compound of formula (I) according to the present invention, is novel, as is the compound of formula (II-B) produced as the intermediate in the reaction scheme 2. Both novel compounds can be represented by the following formula (II), which is within the scope of the present invention,

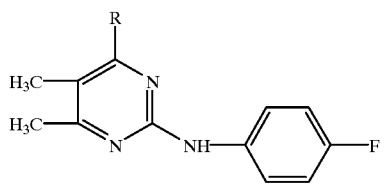

(II)

in which R represents hydroxy or a halogen.

1-Methyl-1,2,3,4-tetrahydroisoquinoline of formula (III), which is also used as the starting material in the reaction scheme 1, is a known compound and can be preapred by known methods (see, for example, International Publication No. WO 94/14795). According to this known method, (R)- or (S)-1-methyl-1,2,3,4-tetrahydroisoquinoline is prepared by reacting (R)- or (S)-methylbenzylamine with α-chloro-α-(methylthio)-acetylchloride and stannous chloride ($SnCl_2$) to produce (R)- or (S)-1-methyl-4-methylthio-1,2,3,4-tetrahydroisoquinolin-3-one, respectively, then reacting the resulting compound with Raney nickel to remove a methylthio group, and finally adding a reducing agent. However, this method is disadvantageous, since α-chloro-α-(methylthio)-acetylchloride, which is used as the starting material, is both unstable and explosive, so that this method cannot be practiced on an industrial scale. Further, since the reaction step is long, the total yield is low, which makes this method uneconomical.

The present inventors have long labored to find a more efficient method for producing 1-methyl-1,2,3,4-tetrahydroisoquinoline. We have discovered that 1-methyl-1,2,3,4-tetrahydroisoquinoline can be employed economically and safely by successively reacting α-methylbenzylamine with 2-bromoethanol, a brominating agent, and a Lewis acid. Such a process for preparing 1-methyl-1,2,3,4-tetrahydroisoquinoline is novel and is encompassed within the scope of the present invention. This novel process for preparing 1-methyl-1,2,3,4-tetrahydroisoquinoline is explained in more detail below.

According to the present invention, 1-methyl-1,2,3,4-tetrahydroisoquinoline of formula (III) can be prepared by reacting α-methylbenzylamine successively with 2-bromoethanol, a brominating agent and Lewis acid. The method of the present invention employs the following reaction scheme 3.

Reaction scheme 3

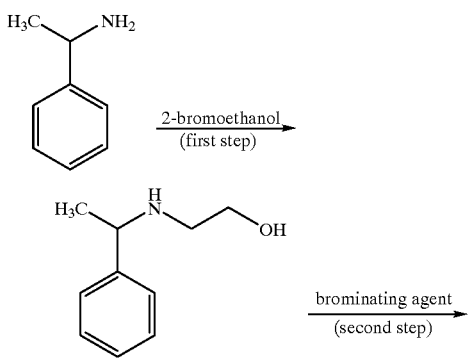

-continued

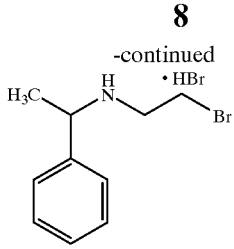

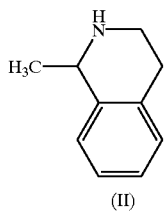

(III)

All of the starting materials and reactants used in the reaction scheme 3 are known compounds and can be obtained as commercial products. In the first step α-methylbenzylamine is reacted with 2-bromoethanol to produce N-(2-hydroxyethyl)-α-methylbenzylamine, which in turn is reacted with the brominating agent to produce N-(2-bromoethyl)-α-methylbenzylamine hydrobromide. In the third step, N-(2-bromoethyl)-α-methylbenzylamine hydrobromide is reacted with a Lewis acid to produce the desired 1-methyl-1,2,3,4-tetrahydroisoquinoline of formula (III).

Reaction solvents which can be used in the first step include acetonitrile, N,N-dimethylformamide, dichloromethane and 1,2-dichloroethane and the reaction temperature is preferably maintained in the range from 40° C. to 60° C. Reaction solvents which can be used in the second step include 1,2-dichloroethane, acetic acid, water and 1,2-dichlorobenzene, and the reaction temperature is preferably maintained in the range from 110° C. to 145° C. Brominating agents which can be used in this reaction include bromine, bromic aicd, aqueous bromic acid solution, and phosphorus tribromide.

Although the first and second steps of the reaction scheme 3 can be practiced by isolating N-(2-hydroxyethyl)-α-methylbenzylamine produced as the intermediate after the first reaction step has been completed, it is preferable to conduct the first and second reaction steps without isolating the intermediate. Thus, the brominating agent is added to the vessel that contains the products of the first reaction step.

Then, N-(2-bromoethyl)-α-methylbenzylamine produced in the second reaction step is cyclized by reaction with a Lewis acid to prepare the desired 1-methyl-1,2,3,4-tetrahydroisoquinoline of formula (III). Reaction solvents which can be used in this reaction include decalin, 1,2-dichloroethane and 1,2-dichlorobenzene and Lewis acids for this cyclization reaction include aluminum (III) chloride, zinc chloride and ferrous chloride.

Since 1-methyl-1,2,3,4-tetrahydroisoquinoline can be economically prepared according to the above method, the desired 5,6-dimethyl-2-(4-fluorophenylamino)-4-(1-methyl-1,2,3,4-tetrahydroisoquinolin-2-yl)-pyrimidine of formula (I) according to the present invention can also be economically prepared using this compound as the reactant.

In order to use the compound of formula (III) in the form of (R)-(+)- or (S)-(−)-isomer as the starting material for preparation of the compound of formula (I) according to the present invention, each isomeric form of the compound of formula (III) can be efficiently prepared using the corresponding (R)-(+)- or (S)-(−)-methylbenzylamine as the starting material used in the method depicted in the reaction scheme 3.

The present invention will be illustrated in detail by the following examples. However, it should be understood that the present invention is not in any manner limited by these examples.

Preparation: 4-fluorophenylguanidine Carbonate 882 g(747 ml) of 32% hydrochloric acid was added to 1000 g(8.9 mole) of 4-fluoroaniline, the mixture was warmed to 87° C., and 780 ml(9.9 mole) of 50% cyanamide solution was added dropwise thereto over 2 hours. The reaction solution was adjusted to pH 2.4 by adding thereto 120 ml of 32% hydrochloric acid, stirred for 3 hours, and cooled to 60° C. Aqueous sodium carbonate solution ($Na_2CO_3$ 578 g/water 1640 ml) was added dropwise to the reaction solution over 30 mlnutes. The reaction mixture was stirred for 40 minutes and then cooled to 15° C. The resulting gray solid product was filtered, washed first with 600 ml of water and then with 2000 ml of ethyl acetate, and finally dried to obtain 1395 g of the title compound, which had a light gray color.

Yield: 81.4% m.p.: 175° C.; NMR(DMSO-$d_6$, ppm): 5.50–6.88(bs, 5H), 6.87(m, 2H), 7.17(m, 2H)

EXAMPLE 1

4-hydroxy-2-(4-fluorophenylamino)-5,6-dimethylpyrimidine 54.5 g(253.2 mmole) of 4-fluorophenylguanidine carbonate produced in the Preparation above was suspended in 50 ml of N,N-dimethylformamide and 37.8 g(262.2 mmole) of ethyl 2-methylacetoacetate and the resulting suspension was refluxed at 140° C. for 3 hours. The reaction solution was diluted again with 100 ml of N,N-dimethylformamide and cooled to 80° C. 160 ml of isopropylalcohol was added thereto and the resulting mixture was stirred for 30 minutes. The resulting solid product was filtered, washed with 150 ml of acetone, and finally dried to obtain 41 g of the title compound.

Yield: 61.4% m.p.: 256° C.; NMR(DMSO-$d_6$, ppm): 1.83(s, 3H), 2.19(s, 3H), 7.18(t, 2H), 7.68 (m, 2H), 9.36(bs, 1H), 10.63(bs, 1H)

EXAMPLE 2

4-chloro-2-(4-fluorophenylamino)-5,6-dimethylpyrimidine 40.5 g(174.1 mmole) of 2-(4-fluorophenylamino)-4-hydroxy-5,6-dimethylpyrimidine produced in Example 1 was suspended in 80 ml of N,N-dimethylformamide and the resulting suspension was heated to 80° C. 31.9 g(19.4 ml, 210.1 mmole) of phosphorus oxychloride was added thereto over one hour at constant temperature of 85° C. The reaction solution was stirred for 30 minutes and then 400 g of ice-water was added thereto with stirring. The mixture was adjusted to pH 11 by adding sodium hydroxide and then the resulting solid product was filtered. The separated solid product was washed with 150 ml of 50% aqueous methanol solution and then dried to obtain 42.3 g of the title compound.

Yield: 96.7% m.p.: 114° C.; NMR(CDCl$_3$, ppm): 2.21(s, 3H), 2.41(s, 3H), 7.01(t, 2H), 7.18(bs, 1H), 7.56(t, 2H)

EXAMPLE 3

4-chloro-2-(4-fluorophenylamino)-5,6-dimethylpyrimidine 1390 g(7.6 mole) of 4-fluorophenylguanidine carbonate produced by the Preparation above was suspended in 1300 ml of N,N-dimethylformamide and 1206 g(8.4 mole) of ethyl 2-methylacetoacetate. The resulting suspension was heated under refluxing for one hour, distilled at normal pressure to 1100 ml and then distilled until the temperature of the reaction solution reached 160° C. 1600 ml of N,N-dimethylformamide was added to the residue and then cooled to 80° C. 1388 g(840 ml, 9.1 mole) of phosphorus oxychloride was added thereto over one hour at constant temperature of 80° C. to 85° C. The reaction solution was stirred for 30 minutes and then diluted with 2000 ml of N,N-dimethyl-formamide. To the diluted reaction solution was added 7000 ml of water over 40 minutes with stirring. The reaction solution was stirred for 4 hours and the resulting solid product was filtered, washed with 1500 ml of 50% aqueous methanol solution and then dried. The dried, yellowish-brown powder thereby obtained was dissolved in 4000 ml of methanol under refluxing and then cooled to 10° C. The resulting solid product was filtered and dried to obtain 1186 g of the title compound.

Yield: 62.4% m.p.: 114° C.; NMR(CDCl$_3$, ppm): 2.21(s, 3H), 2.41(s, 3H), 7.01(t, 2H), 7.18(bs, 1H), 7.56(t, 2H)

EXAMPLE 4

4-bromo-2-(4-fluorophenylamino)-5,6-dimethylpyrimidine 5 g(21.44 mmole) of 2-(4-fluorophenylamino)-4-hydroxy-5,6-dimethylpyrimidine produced in Example 1 was suspended in 40 ml of N,N-dimethylformamide and the resulting suspension was warmed to 65° C. 8.1 g(30 mmole) of phosphorus tribromide was added dropwise thereto over 20 minutes and the resulting mixture was allowed to react at 75° C. for 30 minutes. The reaction solution was cooled to room temperature, poured onto 500 g of ice-water, adjusted to pH 11 with sodium hydroxide solution, stirred for 30 minutes and then adjusted again to pH 5.5 with dilute hydrochloric acid. The resulting yellow solid product was washed with 100 ml of water and the dried to obtain 4.1 g of the title compound.

Yield: 64.58% m.p.: 123° C.; NMR(CDCl$_3$ ppm): 2.21(s, 3H), 2.42(s, 3H), 6.98(t, 2H), 7.24(s, 1H), 7.54(q, 2H)

EXAMPLE 5

1-methyl-1,2,3,4-tetrahydroisoquinoline (1) Preparation of N-(2-hydroxyethyl)-α-methylbenzylamine:

103.08 g(0.86 mole) of α-methylbenzylamine was dissolved in 110 ml of dichloromethane and 127.56 g(1.02 mole) of 2-bromoethanol was added thereto. This mixture was stirred at 52° C. for 50 hours to complete the reaction. The reaction solution was concentrated under reduced pressure and the residue was subjected to fractional distillation to obtain 109 g of the title compound, which had a pale yellow color.

Yield 76.7% m.p.: 60° C./0.5 torr; NMR(CDCl$_3$, ppm): 1.38(d, 3H), 2.40(bs, 1H), 2.61(m, 2H), 3.58(m, 2H), 3.78(q, 1H), 7.18–7.38(m, 5H)

(2) Preparation of N-(2-bromoethyl)-α-methylbenzylamine hydrobromide:

100 g(605.32 mmole) of N-(2-hydroxyethyl)-α-methylbenzylamine produced in Example 5(1) above was suspended in 515 ml of 48% aqueous hydrobromic acid solution and the resulting suspension was reacted at 126° C. for 30 minutes under refluxing. The reaction solution was then distilled for 2 hours under normal pressure at constant temperature and 465 ml of aqueous hydrobromic acid and water, the reaction by-product, was removed. The residue was dissolved in 550 ml of acetone, and 500 ml of ethyl acetate and 670 ml of ether were added thereto. The reaction solution was stirred for 30 minutes, cooled to 0° C. and then allowed to stand for 3 hours. The resulting solid product was filtered, washed with 400 ml of ethyl acetate and then dried to obtain 97 g of the first crop of the title compound. The filtrate was then concentrated. The residue was dissolved in 450 ml of acetone, diluted with 680 ml of ether and then allowed to stand at 0° C. for 12 hours. The resulting solid product was filtered, collected, and washed with 450 ml of ethyl acetate to obtain 32.5 g of the second crop of the title compound.

Yield: 69.23% m.p.: 186–187° C.; NMR(CDCl$_3$, ppm): 1.94(d, 3H), 3.21(m, 2H), 3.82(m, 2H), 4.42(q, 1H), 7.40–7.72(m, 5H), 9.51(bs, 1H), 9.91(bs, 1H)

(3) Preparation of 1-methyl-1,2,3,4-tetrahydroisoquinoline 50.0 g(161.8 mmole) of N-(2-bromoethyl)-α-methylbenzylamine hydrobromide produced in Example 5(2) above was suspended in 450 ml of decalin and then heated to 140° C. 64.70 g(485.4 mmole) of anhydrous aluminum chloride (AlCl$_3$) was added thereto over 40 minutes. The reaction solution was stirred for a further 30 minutes at constant temperature, and then cooled to room temperature. The supernatant was removed and the lower layer was added to 800 g of ice-water with stirring. 150 ml of con. hydrochloric acid was added thereto and the mixture was stirred for 10 minutes. This solution was washed three times, each time with 1000 ml of ethyl acetate, and the resulting aqueous layer was separated, adjusted to pH 12 with sodium hydroxide, and then extracted three times, each time with 2100 ml of ethyl acetate. The extracts were combined, washed with 420 ml of saturated saline, dehydrated with anhydrous magnesium sulfate, and then evaporated under reduced pressure to remove ethyl acetate. The residue was distilled to obtain 18.1 g of the title compound.

Yield 75.99% b.p.: 79–80° C./0.5 torr; NMR(CDCl$_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 6

1-methyl-1,2,3,4-tetrahydroisoquinoline (1) Preparation of N-(2-bromoethyl)-α-methylbenzylamine hydrobromide:

76.61 g(630 mmole) of α-methylbenzylamine was dissolved in 77 ml of dichloromethane and 94.8 g(760 mmole) of 2-bromoethanol was added thereto. This mixture was stirred at 51° C. for 50 hours to complete the reaction. The reaction solution was concentrated under reduced pressure and 286.4 ml(2500 mmole) of 48% aqueous hydrobromic acid solution was added thereto and allowed to react at 126° C. for 30 minutes under refluxing. The reaction solution was then distilled for 2 hours under normal pressure at constant temperature and 250 ml of aqueous hydrobromic acid and water, the reaction by-product, was removed. The residue was dissolved in 350 ml of isopropyl alcohol with refluxing for 30 minutes, and this solution was cooled to 10° C. and then allowed to stand for 3 hours. The resulting solid product was filtered, washed with 50 ml of ethyl acetate and then dried to obtain 128.9 g of the title compound.

Yield: 66.2% m.p.: 186–187° C.; NMR(CDCl$_3$, ppm): 1.94(d, 3H), 3.21(m, 2H), 3.82(m, 2H), 4.42(q, 1H), 7.40–7.72(m, 5H), 9.51(bs, 1H), 9.91(bs, 1H)

(2) Preparation of 1-methyl-1,2,3,4-tetrahydroisoquinoline 10.0 g(30.1 mmole) of N-(2-bromoethyl)-α-methylbenzylamine hydrobromide produced in Example 6(1) above was suspended in 60 ml of 1,2-dichlorobenzene and then heated to 145° C. 13.47 g(96.54 mmole) of anhydrous aluminum chloride was added thereto over 40 minutes. The reaction solution was stirred for a further 30 minutes at constant temperature, cooled to room temperature and poured onto 250 g of ice-water with stirring. 30 ml of con. hydrochloric acid was added thereto and the mixture was stirred for 10 minutes. This solution was washed three times, each time with 130 ml of dichloromethane, and the resulting aqueous layer was separated, adjusted to pH 12 with sodium hydroxide and then extracted three times, each time with 250 ml of ethyl acetate. The extracts were combined, washed with 40 ml of saturated saline, dehydrated with anhydrous magnesium sulfate and then evaporated under reduced pressure to remove ethyl acetate. The residue was distilled to obtain 2.90 g of the title compound.

Yield: 65.39% b.p.: 79–80° C./0.5 torr; NMR(CDCl$_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 7

1-methyl-1,2,3,4-tetrahydroisoquinoline 200 g(647.17 mmole) of N-(2-bromoethyl)-α-methylbenzylamine hydrobromide produced in Example 5(2) or Example 6(1) above was suspended in 700 ml of decalin and then heated to 150° C. 261.5 g(1961 mmole) of anhydrous aluminum chloride was added thereto over 40 minutes. The reaction solution was stirred for s further 30 minutes at constant temperature and then cooled to room temperature. The supernatant was removed and the lower layer was poured onto 3500 g of ice-water with stirring. 210 ml of con. hydrochloric acid was added thereto and the mixture was stirred for 10 minutes. This solution was washed three times, each time with 2500 ml of ethyl acetate, and then the aqueous layer was separated, adjusted to pH 12 with sodium hydroxide, and then extracted three times, each time with 3000 ml of ethyl acetate. The extracts were combined, washed with 550 ml of saturated saline, dehydrated with anhydrous magnesium sulfate, and then evaporated under reduced pressure to remove ethyl acetate. The residue was distilled to obtain 78.9 g of the title compound.

Yield: 82.8% b.p.: 79–80° C./0.5 torr; NMR(CDCl$_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 8

(R)-(+)-1-methyl-1,2,3,4-tetrahydroisoquinoline (1) Preparation of (R)-(+)-N-(2-hydroxyethyl)-α-methylbenzylamine:

51.45 g(0.43 mmole) of (R)-(+)-α-methylbenzylamine was dissolved in 52 ml of dichloromethane and 63.78 g(0.51 mmole) of 2-bromoethanol was added thereto. This mixture was stirred at 51° C. for 50 hours to complete the reaction. The reaction solution was concentrated under reduced pressure and the residue was subjected to fractional distillation to obtain 54 g of the title compound having pale yellow color.

Yield: 76% m.p.: 60° C./0.5 torr; $[\alpha]_D^{20}$: +55° (c=1, in CHCl$_3$); NMR(CDCl$_3$, ppm): 1.38(d, 3H), 2.40(bs, 1H), 2.61(m, 2H), 3.58(m, 2H), 3.78(q, 1H), 7.18–7.38(m, 5H)

(2) Preparation of (R)-(+)-N-(2-bromoethyl)-α-methylbenzylamine hydrobromide:

11.0 g(66.58 mmole) of (R)-(+)-N-(2-hydroxyethyl)-α-methylbenzylamine produced in Example 8(1) above was suspended in 52 ml of 48% aqueous hydrobromic acid solution and the resulting suspension was reacted at 126° C. for 30 minutes under refluxing. The reaction solution was distilled for 2 hours under normal pressure at constant temperature and 47 ml of aqueous hydrobromic acid and water, the reaction by-product, was removed. The residue was dissolved in 55 ml of acetone, and 50 ml of ethyl acetate and 70 ml of ether were added thereto. The reaction solution was stirred for 30 minutes, cooled to 0° C. and then allowed to stand for 3 hours. The resulting solid product was filtered, washed with 30 ml of ethyl acetate and then dried to obtain 10 g of the first crop of the title compound. The filtrate was then concentrated. The residue was dissolved in 60 ml of ethanol and the resulting mixture was concentrated under reduced pressure. The residue was dissolved in 50 ml of acetone, diluted with 70 ml of ether and then allowed to stand at 0° C. for 12 hours. The resulting solid product was filtered, collected and washed with 30 ml of ethyl acetate to obtain 3.1 g of the second crop of the title compound.

Yield: 64% m.p.: 186–187° C.; $[\alpha]_D^{20}$: +32.1° (c=1, in $CHCl_3$); NMR($CDCl_3$, ppm): 1.94(d, 3H), 3.21(m, 2H), 3.82(m, 2H), 4.42(q, 1H), 7.40–7.72(m, 5H), 9.51(bs, 1H), 9.91(bs, 1H)

(3) Preparation of (R)-(+)-1-methyl-1,2,3,4-tetrahydroisoquinoline 5.0 g(16.18 mmole) of (R)-(+)-N-(2-bromoethyl)-α-methylbenzylamine hydrobromide produced in the above (2) was suspended in 50 ml of decalin and the resulting suspension was heated to 140° C. 6.470 g (48.54 mmole) of anhydrous aluminum chloride ($AlCl_3$) was added thereto over 40 minutes. The reaction solution was stirred for further 30 minutes at constant temperature, and cooled to room temperature. The supernatant was removed and the lower layer was added to 70 g of ice-water with stirring. 20 ml of con. hydrochloric acid was added thereto and the mixture was stirred for 10 minutes. This solution was washed three times, each time with 100 ml of ethyl acetate, and the resulting aqueous layer was separated, adjusted to pH 12 with sodium hydroxide and then extracted three times, each time with 250 ml of ethyl acetate. The extracts were combined, washed with 40 ml of saturated saline, dehydrated with anhydrous magnesium sulfate and then evaporated under reduced pressure to remove ethyl acetate. The residue was distilled to obtain 1.70 g of the title compound.

Yield: 71.4% b.p.: 79–80° C./0.5tor; $[\alpha]_D^{20}$: +85.5° (c=1, in $CHCl_3$); NMR($CDCl_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 9

(R)-(+)-1-methyl-1,2,3,4-tetrahydroisoquinoline
(1) Preparation of (R)-(+)-N-(2-bromoethyl)-α-methylbenzylamine hydrobromide:

76.61 g(630 mmole) of (R)-(+)-α-methylbenzylamine was dissolved in 77 ml of dichloromethane and 94.8 g(760 mmole) of 2-bromoethanol was added thereto. This mixture was stirred at 51° C. for 50 hours to complete the reaction. The reaction solution was concentrated under reduced pressure and 286.4 ml(2500 mmole) of 48% aqueous hydrobromic acid solution was added thereto and then allowed to react at 126° C. for 30 minutes under refluxing. The reaction solution was then distilled for 2 hours under normal pressure at constant temperature and 250 ml of aqueous hydrobromic acid and water, the reaction by-product, was removed. The residue was dissolved in 350 ml of isopropyl alcohol with refluxing for 30 minutes, and this solution was cooled to 10° C. and then allowed to stand for 3 hours. The resulting solid product was filtered, washed with 50 ml of ethyl acetate, and then dried to obtain 127.5 g of the title compound.

Yield: 65.5% m.p.: 186–187° C.; $[\alpha]_D^{20}$: +32.1° (c=1, in $CHCl_3$); NMR($CDCl_3$, ppm): 1.94(d, 3H), 3.21(m, 2H), 3.82(m, 2H), 4.42(q, 1H), 7.40–7.72(m, 5H), 9.51(bs, 1H), 9.91(bs, 1H)

(2) Preparation of (R)-(+)-1-methyl-1,2,3,4-tetrahydroisoquinoline 10.0 g(30.1 mmole) of (R)-(+)-N-(2-bromoethyl)-α-methylbenzylamine hydrobromide produced in Example 9(1) above was suspended in 60 ml of 1,2-dichlorobenzene and then heated to 145° C. 13.47 g(96.54 mmole) of anhydrous aluminum chloride ($AlCl_3$) was added thereto over 40 minutes. The reaction solution was stirred for further 30 minutes at same temperature, cooled to room temperature and poured onto 250 g of ice-water with stirring. 30 ml of con. hydrochloric acid was added thereto and the mixture was stirred for 10 minutes. This solution was washed three times, each time with 130 ml of dichloromethane, and the resulting aqueous layer was separated, adjusted to pH 12 with sodium hydroxide and then extracted three times, each time with 250 ml of ethyl acetate. The extracts were combined, washed with 40 ml of saturated saline, dehydrated with anhydrous magnesium sulfate, and then evaporated under reduced pressure to remove ethyl acetate. The residue was distilled to obtain 3.06 g of the title compound.

Yield: 69% b.p.: 79–80° C./0.5 torr; $[\alpha]_D^{20}$: +85.5° (c=1, in $CHCl_3$); NMR($CDCl_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 10

(R)-(+)-1-methyl-1,2,3,4-tetrahydroisoquinoline 73.45 g(240 mmole) of (R)-(+)-N-(2-bromoethyl)-α-methylbenzylamine hydrobromide produced in Example 9(1) above was suspended in 260 ml of decalin and the resulting suspension was heated to 150° C. 95.10 g(710 mmole) of anhydrous aluminum chloride was added thereto over 40 minutes. The reaction solution was stirred for a further 30 minutes at same temperature and then cooled to room temperature. The supernatant was removed and the lower layer was poured onto 1600 g of ice-water with stirring. 70 ml of con. hydrochloric acid was added thereto and the resulting mixture was stirred for 10 minutes. This solution was washed three times, each time with 700 ml of ethyl acetate, and the resulting aqueous layer was separated, adjusted to pH 12 with sodium hydroxide, and extracted three times, each time with 900 ml of ethyl acetate. The extracts were combined, washed with 200 ml of saturated saline, dehydrated with anhydrous magnesium sulfate, and evaporated under reduced pressure to remove ethyl acetate. The residue was distilled to obtain 28.2 g of the title compound.

Yield: 79.7% b.p.: 79–80° C./0.5 torr; $[\alpha]_D^{20}$: +85.5° (c=1, in $CHCl_3$); NMR($CDCl_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 11

(S)-(−)-1-methyl-1,2,3,4-tetrahydroisoquinoline
(1) Preparation of (S)-(−)-N-(2-hydroxyethyl)-α-methylbenzylamine:

108.23 g(0.903 mmole) of (S)-(−)-α-methylbenzylamine was dissolved in 140 ml of dichloromethane and 144.0 g(1.071 mmole) of 2-bromoethanol was added thereto. This mixture was stirred at 51° C. for 52 hours to complete the reaction. The reaction solution was concentrated under reduced pressure and the residue was subjected to fractional distillation to obtain 117.4 g of the title compound, which had a pale yellow color.

Yield: 78.7% m.p.: 60° C./0.5 torr; $[\alpha]_D^{20}$: −55° (c=1, in CHCl$_3$); NMR(CDCl$_3$, ppm): 1.38(d, 3H), 2.40(bs, 1H), 2.61(m, 2H), 3.58(m, 2H), 3.78(q, 1H), 7.18–7.38(m, 5H)

(2) Preparation of (S)-(−)-N-(2-bromoethyl)-α-methylbenzylamine hydrobromide:

22.1 g(133.16 mmole) of (S)-(−)-N-(2-hydroxyethyl)-α-methylbezylamine produced in Example 11(1) above was suspended in 105 ml of 48% aqueous hydrobromic acid solution and the resulting suspension was reacted at 126° C. for 30 minutes under refluxing. Then, the reaction solution was distilled for 2 hours under normal pressure at constant temperature and 95 ml of aqueous hydrobromic acid and water, the reaction by-product, was removed. The residue was dissolved in 112 ml of acetone, and 100 ml of ethyl acetate and 150 ml of ether were added thereto. The reaction solution was stirred for 30 minutes, cooled to 0° C. and then allowed to stand for 3 hours. The resulting solid product was filtered, washed with 70 ml of ethyl acetate and then dried to obtain 20 g of the first crop of the title compound. The filtrate was then concentrated. The residue was dissolved in 130 ml of ethanol and then concentrated under reduced pressure. The residue was dissolved in 104 ml of acetone, diluted with 143 ml of ether, and then allowed to stand at 0° C. for 12 hours. The resulting solid product was filtered, collected and washed with 75 ml of ethyl acetate to obtain 6.7 g of the second crop of the title compound.

Yield: 64.8% m.p.: 186–187° C.; $[\alpha]_D^{20}$: −32.1° (c=1, in CHCl$_3$); NMR(CDCl$_3$, ppm): 1.94(d, 3H), 3.21(m, 2H), 3.82(m, 2H), 4.42(q, 1H), 7.40–7.72(m, 5H), 9.51(bs, 1H), 9.91(bs, 1H)

(3) Preparation of (S)-(−)-1-methyl-1,2,3,4-tetrahydroisoquinoline 5.0 g(16.18 mmole) of (S)-(−)-N-(2-bromoethyl)-α-methylbenzylamine hydrobromide produced in Example (2) above was suspended in 50 ml of decalin and then heated to 140° C. 6.47 g(48.54 mmole) of anhydrous aluminum chloride (AlCl$_3$) was added thereto over 40 minutes. The reaction solution was stirred for further 30 minutes at constant temperature, and cooled to room temperature. The supernatant was removed and the lower layer was added to 70 g of ice-water with stiring. 20 ml of con. hydrochloric acid was added thereto and the mixture was stirred for 10 minutes. This solution was washed three times, each time with 100 ml of ethyl acetate, and the aqueous layer was separated, adjusted to pH 12 with sodium hydroxide and then extracted three times, each time with 250 ml of ethyl acetate. The extracts were combined, washed with 40 ml of saturated saline, dehydrated with anhydrous magnesium sulfate, and then evaporated under reduced pressure to remove ethyl acetate. The residue was distilled to obtain 1.75 g of the title compound.

Yield: 73.5% b.p.: 79–80° C./0.5 torr; $[\alpha]_D^{20}$: −85.5° (c=1, in CHCl$_3$); NMR(CDCl$_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 12

(S)-(−)-1-methyl-1,2,3,4-tetrahydroisoquinoline
(1) Preparation of (S)-(−)-N-(2-bromoethyl)-α-methylbenzylamine hydrobromide:

176.20 g(1449 mmole) of (S)-(−)-α-methylbenzylamine was dissolved in 185 ml of dichloromethane and 218.04 g(1748 mmole) of 2-bromoethanol was added thereto. This mixture was stirred at 51° C. for 50 hours to complete the reaction. The reaction solution was concentrated under reduced pressure and 658 ml(5750 mmole) of 48% aqueous hydrobromic acid solution was added thereto and the solution thereby obtained was allowed to react at 126° C. for 30 minutes under refluxing. The reaction solution was distilled for 2 hours under normal pressure at constant temperature to remove 580 ml of water as the by-product and aqueous hydrobromic acid solution. The residue was dissolved in 760 ml of isopropyl alcohol with refluxing for 30 minutes, and this solution was cooled to 10° C. and then allowed to stand for 3 hours. The resulting solid product was filtered, washed with 150 ml of ethyl acetate and then dried to obtain 306.5 g of the title compound.

Yield: 68.4% m.p.: 185° C.; $[\alpha]_D^{20}$: −32.1° (c=1, in CHCl$_3$); NMR(CDCl$_3$, ppm): 1.94(d, 3H), 3.21(m, 2H), 3.82(m, 2H), 4.42(q, 1H), 7.40–7.72(m, 5H), 9.51(bs, 1H), 9.91(bs, 1H)

(2) Preparation of (S)-(−)-1-methyl-1,2,3,4-tetrahydroisoquinoline 10.0 g(30.1 mmole) of (S)-(−)-N-(2-bromoethyl)-α-methylbenzylamine hydrobromide produced in Example 12(1) above was suspended in 60 ml of 1,2-dichlorobenzene and then heated to 145° C. 13.47 g(96.54 mmole) of anhydrous aluminum chloride (AlCl$_3$) was added thereto over 40 minutes. The reaction solution was stirred for further 30 minutes at constant temperature, cooled to room temperature and poured onto 250 g of ice-water with stirring. 30 ml of con. hydrochloric acid was added thereto and the mixture was stirred for 10 minutes. This solution was washed three times, each time with 130 ml of dichloromethane, and the resulting aqueous layer was separated, adjusted to pH 12 with sodium hydroxide, and then extracted three times, each time with 250 ml of ethyl acetate. The extracts were combined, washed with 40 ml of saturated saline, dehydrated with anhydrous magnesium sulfate, and then evaporated under reduced pressure to remove ethyl acetate. The residue was distilled to obtain 3.10 g of the title compound.

Yield: 69.96% b.p.: 79–80° C./0.5 torr; $[\alpha]_D^{20}$: −85.5° (c=1, in CHCl$_3$); NMR(CDCl$_3$, ppm) 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

EXAMPLE 13

(S)-(−)-1-methyl-1,2,3,4-tetrahydroisoquinoline 73.45 g(240 mmole) of (S)-(−)-N-(2-bromoethyl)-α-methylbenzylamine hydrobromide produced in Example 12(1) above was suspended in 260 ml of decalin and the resulting suspension was heated to 150° C. 95.10 g(710 mmole) of anhydrous aluminum chloride was added thereto over 40 minutes. The reaction solution was stirred for a further 30 minutes at constant temperature and then cooled to room temperature. The supernatant was removed and the lower layer was poured onto 1600 g of ice-water with stirring. 70 ml of con. hydrochloric acid was added thereto and the mixture was stirred for 10 minutes. This solution was washed three times, each time with 700 ml of ethyl acetate, and then the aqueous layer was separated, adjusted to pH 12 with sodium hydroxide, and then extracted three times, each time with 900 ml of ethyl acetate. The extracts were combined, washed with 200 ml of saturated saline, dehydrated with anhydrous magnesium sulfate, and then evaporated under reduced pressure to remove ethyl acetate. The residue was distilled to obtain 27.6 g of the title compound.

Yield: 78.1% b.p.: 79–80° C./0.5 torr; $[\alpha]_D^{20}$: −85.5° (c=1, in $CHCl_3$); NMR($CDCl_3$, ppm): 1.59(d, 3H), 2.14(s, 1H), 2.76–3.02(m, 2H), 3.10–3.22(m, 1H), 3.34–3.45(m, 1H), 4.22(q, 1H), 7.18–7.31(m, 4H)

Preparation of 5,6-dimethyl-2-(4-fluorophenylamino)-4-(1-methyl-1,2,3,4-tetrahydroisoquinolin-2-yl)pyrimidine and its hydrochloride In Examples 14 to 20, inclusive, 1-methyl-1,2,3,4-tetrahydroisoquinoline prepared according to the method disclosed in International Publication No. WO 94/14795 was used as the reactant.

EXAMPLE 14

2.65 g(27 mmole) of potassium acetate and 4.0 g(26.9 mmole) of 1-methyl-1,2,3,4-tetrahydroisoquinoline were added to 85 ml of n-hexanol and then warmed to 80° C. 6.17 g(24.5 mmole) of 4-chloro-2-(4-fluorophenylamino)-5,6-dimethylpyrimidine was added thereto and then reacted at 140° C. for 28 hours under refluxing to prepare 5,6-dimethyl-2-(4-fluorophenylamino)-4-(1-methyl-1,2,3,4-tetrahydroisoquinolin-2-yl)pyrimidine.

The reaction solution was cooled to room temperature, diluted with 20 ml of acetone and then added dropwise to 120 ml of water with stirring. After it had been stirred for 2 hours, the resulting solid product was filtered, washed with 30 ml of water, dissolved in 150 ml of dichloromethane and then washed successively with 20 ml of 4N-HCl, 20 ml of water and then 20 ml of 4N-sodium hydroxide solution. The dichloromethane layer was dehydrated with anhydrous magnesium sulfate, concentrated under reduced pressure, and then diluted with 100 ml of ethanol. To this reaction solution was added 30 g of conc. hydrochloric acid, and the mixture thereby obtained was stirred for 5 hours. The resulting solid product was filtered, washed with 20 ml of ethanol and then dried to obtain 6.1 g of purified 5,6-dimethyl-2-(4-fluorophenylamino)-4-(1-methyl-1,2,3,4-tetrahydroisoquinolin-2-yl)pyrimidine hydrochloride.

Yield: 62.4% m.p.: 255° C.; NMR($CDCl_3$, ppm) 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 15

8.12 g(11.2 ml, 80.3 mmole) of triethylamine, 30 ml of n-butanol and 6.58 g(44.1 mmole) of 1-methyl-1,2,3,4-tetrahydroisoquinoline were added to 40 ml of ethylene glycol. 10.1 g(40.1 mmole) of 4-chloro-2-(4-fluorophenylamino)-5,6-dimethylpyrimidine was added thereto and then reacted at 130° C. for 30 hours under refluxing to prepare 5,6-dimethyl-2-(4-fluorophenylamino)-4-(1-methyl-1,2,3,4-tetrahydroisoquinolin-2-yl)-pyrimidine. This product was treated according to the procedure detailed in Example 14 to obtain 14.7 g of purified 5,6-dimethyl-2-(4-fluorophenylamino)-4-(1-methyl-1,2,3,4-tetrahydroisoquinolin-2-yl)pyrimidine hydrochloride.

Yield 91% m.p.: 256° C.; NMR($CDCl_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 16

45 ml of triethylamine, 50 ml of n-butanol and 32 g(217 mmole) of 1-methyl-1,2,3,4-tetrahydroisoquinoline were added to 150 ml of ethylene glycol. 51.3 g(203.8 mmole) of 4-chloro-2-(4-fluorophenylamino)-5,6-dimethylpyrimidine was added thereto and then reacted at 135° C. for 28 hours under refluxing to prepare 5,6-dimethyl-2-(4-fluorophenylamino)-4-(1-methyl-1,2,3,4-tetrahydroisoquinolin-2-yl)pyrimidine. This product was treated according to the procedure detailed in Example 14 to obtain 66 g of purified 5,6-dimethyl-2-(4-fluorophenylamino)-4-(1-methyl-1,2,3,4-tetrahydroisoquinolin-2-yl)pyrimidine hydrochloride.

Yield: 81.1% m.p.: 256° C.; NMR($CDCl_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 17

75 ml of triethylamine and 65 g(442 mmole) of 1-methyl-1,2,3,4-tetrahydroisoquinoline were added to 100 ml of 1,2-propylene glycol. 100.9 g(0.40 mmole) of 4-chloro-2-(4-fluorophenylamino)-5,6-dimethylpyrimidine was added thereto and then reacted at 120° C. for 64 hours under refluxing to prepare 5,6-dimethyl-2-(4-fluorophenylamino)-4-(1-methyl-1,2,3,4-tetrahydroisoquinolin-2-yl)pyrimidine. This product was treated according to the procedure detailed in Example 14 to obtain 91 g of purified 5,6-dimethyl-2-(4-fluorophenylamino)-4-(1-methyl-1,2,3,4-tetrahydroisoquinolin-2-yl)pyrimidine hydrochloride.

Yield: 57.1% m.p.: 258° C.; NMR($CDCl_3$, ppm) 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 18

720 ml of triethylamine and 695 g(4.72 mmole) of 1-methyl-1,2,3,4-tetrahydroisoquinoline were added to 2100 ml of 1,2-propylene glycol. 1179 g(4.68 mmole) of 4-chloro-2-(4-fluorophenylamino)-5,6-dimethylpyrimidine was added thereto and the mixture thereby obtained was reacted at 130° C. for 58 hours to prepare 5,6-dimethyl-2-(4-fluorophenylamino)-4-(1-methyl-1,2,3,4-tetrahydroisoquinolin-2-yl)pyrimidine. This product was treated according to the procedure detailed in Example 14 to obtain 1250 g of purified 5,6-dimethyl -2-(4-fluorophenyamino)-4-(1-methyl -1,2,3,4-tetrahydroisoquinolin-2-yl)pyrimidine hydrochloride.

Yield: 66.9% m.p.: 258° C.; NMR($CDCl_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 19

110 ml of n-butanol, 240 ml of triethylamine and 236 g(1.60 mmole) of 1-methyl-1,2,3,4-tetrahydroisoquinoline were added to 600 ml of ethylene glycol. 400 g(1.59 mmole) of 4-chloro-2-(4-fluorophenylamino)-5,6-dimethylpyrimidine was added thereto and then reacted at 140° C. for 48 hours to prepare 5,6-dimethyl-2-(4-fluorophenylamino)-4-(1-methyl-1,2,3,4-tetrahydroisoquinolin-2-yl)pyrimidine. This product was treated according to the procedure detailed in Example 14 to obtain 485 g of purified 5,6-dimethyl -2-(4-fluorophenylamino)-4-(1-methyl-1,2,3,4-tetrahydroisoquinolin-2-yl)pyrimidine hydrochloride.

Yield: 76.5% m.p.: 257° C.; NMR($CDCl_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (sd, 1H), 13.43(bs, 1H)

EXAMPLE 20

240 ml of triethylamine and 9.7 g(65.8 mmole) of 1-methyl-1,2,3,4-tetrahydroisoquinoline were added to 25 ml of 1,2-propylene glycol. Then, 15 g(51 mmole) of 4-bromo-2-(4-fluorophenylamino)-5,6-dimethylpyrimidine was added thereto and the mixture thereby obtained was reacted at 110° C. for 28 hours. The resulting product was treated according to the procedure detailed in Example 14 to obtain 15.86 g of purified 5,6-dimethyl-2-(4-fluorophenylamino)-4-(1-methyl -1,2,3,4-tetrahydroisoquinolin-yl)pyrimidine hydrochloride.

Yield: 78% m.p.: 257° C.; NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 21

8.12 g(11.2 ml, 80.3 mmole) of triethylamine, 30 ml of n-butanol and 6.58 g(44.1 mmole) of 1-methyl-1,2,3,4-tetrahydroisoquinoline as prepared in Example 5 were added to 40 ml of ethylene glycol. 10.1 g(40.1 mmole) of 4-chloro-2-(4-fluorophenylamino)-5,6-dimethylpyrimidine was added thereto and then reacted at 130° C. for 30 hours under refluxing to prepare 5,6-dimethyl-2-(4-fluorophenylamino)-4-(1-methyl-1,2,3,4-tetrahydroisoquinolin-2-yl)pyrimidine.

The reaction solution was cooled to room temperature, diluted with 30 ml of acetone and then added dropwise to 200 ml of water with stirring. After it had been stirred for 2 hours, the resulting solid product was filtered, washed with 60 ml of water, dissolved in 250 ml of dichloromethane and washed successively first with 35 ml of 4N-HCl, 35 ml of water and then with 40 ml of 4N-sodium hydroxide solution. The dichloromethane layer was dehydrated with anhydrous magnesium sulfate, concentrated under reduced pressure, and then diluted with 200 ml of ethanol. To this reaction solution was added 45 g of concentrated hydrochloric acid, and the mixture was stirred for 5 hours. The resulting solid product was filtered, washed with 30 ml of ethanol and then dried to obtain 9.82 g of purified 5,6-dimethyl-2-(4-fluorophenylamino)-4-(1-methyl-1,2,3,4-tetrahydroisoquinolin-2-yl)pyrimidine hydrochloride.

Yield: 66.53% m.p.: 255° C.; NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 22

75 ml of triethylamine and 65 g(442 mmole) of 1-methyl-1,2,3,4-tetrahydroisoquinoline as prepared in Example 7 were added to 100 ml of 1,2-propylene glycol. 100.9 g(0.40 mmole) of 4-chloro-2-(4-fluorophenylamino)-5,6-dimethylpyrimidine was added thereto and then reacted at 120° C. for 64 hours to prepare 5,6-dimethyl-2-(4-fluorophenylamino)-4-(1-methyl-1,2,3,4-tetrahydroisoquinolin-2-yl)pyrimidine. This product was treated according to the procedure detailed in Example 21 to obtain 95.1 g of purified 5,6-dimethyl-2-(4-fluorophenylamino)-4-(1-methyl-1,2,3,4-tetrahydroisoquinolin-2-yl)pyrimidine hydrochloride.

Yield: 59.67% m.p.: 258° C.; NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 23

14 ml of triethylamine and 9.7 g(65.8 mmole) of 1-methyl-1,2,3,4-tetrahydroisoquinoline as prepared in Example 7 were added to 25 ml of 1,2-propylene glycol. 15 g(51 mmole) of 4-bromo-2-( 4-fluorophenylamino)-5,6-dimethylpyrimidine was added thereto and then reacted at 120° C. for 28 hours to prepare 5,6-dimethyl-2-(4-fluorophenylamino)-4-(1-methyl-1,2,3,4-tetrahydroisoquinolin-2-yl)pyrimidine. This product was treated according to the procedure detailed in Example 21 to obtain 14.9 g of purified 5,6-dimethyl-2-(4-fluorophenylamino)-4-(1-methyl -1,2,3,4-tetrahydroisoquinolin-2-yl)pyrimidine hydrochloride.

Yield: 73.28% m.p.: 257° C.; NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61 (m, 2H), 10.33 (s, 1H), 13.43(bs, 1H)

EXAMPLE 24

8.12 g(11.2 ml, 80.3 mmole) of triethylamine, 30 ml of n-butanol and 6.58 g(44.1 mmole) of (R)-(+)-1-methyl-1,2,3,4-tetrahydroisoquinoline as prepared in Example 9 were added to 40 ml of ethylene glycol. 10.1 g (40.1 mmole) of 4-chloro-2-(4-fluorophenylamino)-5,6-dimethylpyrimidine was added thereto and then reacted at 130° C. for 30 hours under refluxing to prepare 5,6-dimethyl-2-(4-fluorophenylamino)-4-(1-methyl-1,2,3,4-tetrahydroisoquinolin-2-yl)pyrimidine.

The reaction solution was cooled to room temperature, diluted with 30 ml of acetone and then added dropwise to 200 ml of water with stirring. After it had been stirred for 2 hours, the resulting solid product was filtered, washed with 60 ml of water, dissolved in 250 ml of dichloromethane and then washed successively with 35 ml of 4N-HCl, 35 ml of water and then 40 ml of 4N-sodium hydroxide solution. The dichloromethane layer was dehydrated with anhydrous magnesium sulfate, concentrated under reduced pressure, and then diluted with 200 ml of ethanol. To this reaction solution was added 45 g of conc. hydrochloric acid, and the resulting mixture was stirred for 5 hours. The resulting solid product was filtered, washed with 30 ml of ethanol and then dried to obtain 9.21 g of purified (R)-(+)-5,6-dimethyl-2-(4-fluorophenylamino)-4-(1-methyl-1,2,3,4-tetrahydroisoquinolin-2-yl)pyrimidine hydrochloride.

Yield: 62.4% m.p.: 255° C.; $[\alpha]_D^{20}$: +250° (c=1, in CHCl$_3$); NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61(m, 2H), 10.33 (s, 1H), 13.43(bs, 1H)

EXAMPLE 25

23 ml of triethylamine and 16 g(108.5 mmole) of (R)-(+)-1-methyl-1,2,3,4-tetrahydroisoquinoline as prepared in Example 10 were added to 75 ml of ethylene glycol. 25.7 g(101.8 mmole) of 4-chloro-2-(4-fluorophenylamino)-5,6-dimethylpyrimidine was added thereto and the mixture thereby obtained was reacted at 135° C. for 28 hours under refluxing to prepare (R)-(+)-5,6-dimethyl-2-(4-fluorophenylamino)-4-(1-methyl-1,2,3,4-tetrahydroisoquinolin-2-yl)pyrimidine. This product was treated according to the procedure detailed in Example 24 to obtain 33 g of purified 5,6-dimethyl-2-(4-fluorophenylamino)-4-(11-methyl-1,2,3,4-tetrahydroisoquinolin-2-yl)-pyrimidine hydrochloride.

Yield: 81.1% m.p.: 257° C.; $[\alpha]_D^{20}$: +250° (c=1, in CHCl$_3$); NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61(m, 2H), 10.33 (s, 1H), 13.43(bs, 1H)

EXAMPLE 26

14 ml of triethylamine and 9.7 g(65.8 mmole) of (R)-(+)-1-methyl- 1,2,3,4-tetrahydroisoquinoline as prepared in Example 10 were added to 25 ml of 1,2-propylene glycol. 15 g(51 mmole) of 4-bromo-2-(4-fluorophenylamino)-5,6- dimethylpyrimidine was added thereto and the mixture thereby obtained was reacted at 120° C. for 28 hours. The reaction product was thentreated according to the procedure detailed in Example 24 to obtain 16.2 g of purified 5,6-dimethyl-2-(4-fluorophenylamino)-4-(1-methyl-1,2,3,4-tetrahydroisoquinolin-2-yl)pyrimidine hydrochloride.

Yield: 79.97% m.p.: 257° C.; $[\alpha]_D^{20}$: +250° (c=1, in CHCl$_3$); NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61(m, 2H), 10.33(s, 1H), 13.43(bs, 1H)

EXAMPLE 27

8.12 g(11.2 ml, 80.3 mmole) of triethylamine, 30 ml of n-butanol and 6.58 g(44.1 mmole) of (S)-(-)-1-methyl-1,2,3,4-tetrahydroisoquinoline as prepared in Example 13 were added to 40 ml of ethylene glycol. 10.1 g (40.1 mmole) of 4-chloro-2-(4-fluorophenylamino)-5,6-dimethylpyrimidine was added thereto and then reacted at 130° C. for 30 hours under refluxing to prepare (S)-(-)-5,6-dimethyl-2-(4-fluorophenylamino)-4-(1-ethyl-1,2,3,4-tetrahydroisoquinolin-2-yl)pyrimidine.

The reaction solution was cooled to room temperature, diluted with 30 ml of acetone and then added dropwise to 200 ml of water with stirring. After it had been stirred for 2 hours, the resulting solid product was filtered, washed with 60 ml of water, dissolved in 250 ml of dichloromethane and washed successively with 35 ml of 4N-HCl, 35 ml of water and 40 ml of 4N-sodium hydroxide solution. The dichloromethane layer was dehydrated with anhydrous magnesium sulfate, concentrated under reduced pressure, and then diluted with 200 ml of ethanol. To this reaction solution was added 45 g of conc. hydrochloric acid, and the mixture was stirred for 5 hours. The resulting solid product was filtered, washed with 30 ml of ethanol and then dried to obtain 8.95 g of purified (S)-(-)-5,6-dimethyl-2-(4-fluorophenylamino)-4-(1-methyl-1,2,3,4-tetrahydroisoquinolin-2-yl)pyrimidine hydrochloride.

Yield: 60.6% m.p.: 255° C.; $[\alpha]_D^°$: -250° (c=1, in CHCl$_3$); NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38(q, 1H), 7.25(m, 6H), 7.61(m, 2H), 10.33 (s, 1H), 13.43(bs, 1H)

EXAMPLE 28

15 ml of triethylamine and 9.7 g(65.8 mmole) of (S)-(-)-1-methyl-1,2,3,4-tetrahydroisoquinoline as prepared in Example 13 were added to 25 ml of 1,2-propylene glycol. 15 g(51 mmole) of 4-bromo-2-(4-fluorophenylamino)-5,6-dimethylpyrimidine was added thereto and then reacted at 110° C. for 38 hours. The reaction product was treated according to the procedure detailed in Example 27 to obtain 15.86 g of purified 5,6-dimethyl-2-(4-fluorophenylamino)-4-(1-methyl-1,2,3,4-tetrahydroisoquinolin-2-yl)pyrimidine hydrochloride.

Yield: 78% m.p.: 257° C.; $[\alpha]_D^{20}$: -250° (c=1, in CHCl$_3$); NMR(CDCl$_3$, ppm): 1.58(d, 3H), 2.21(s, 3H), 2.38(s, 3H), 2.84(m, 1H), 3.12(m, 1H), 3.61(m, 2H), 4.23(m, 1H), 5.38 (q, 1H), 7.25(m, 6H), 7.61(m, 2H), 10.33 (s, 1H), 13.43(bs, 1H)

What is claimed is:

1. A process for preparing 5,6-dimethyl-2-(4-fluorophenyl-amino)-4-(1-methyl-1,2,3,4-tetrahydroisoquinolin-2-yl) pyrimidine represented by the formula (I),

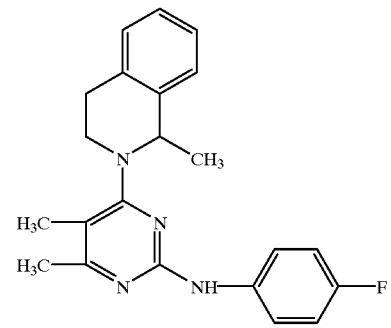

and its acid addition salts, in which a pyrimidine derivative represented by the formula (II-A),

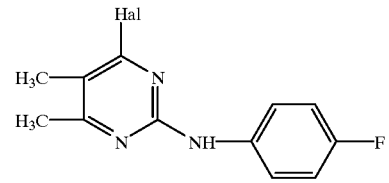

in which Hal represents a halogen atom, is reacted with 1-methyl-1,2,3,4-tetrahydroisoquinoline represented by the formula (III),

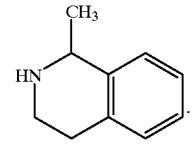

2. The process as defined in claim 1, in which the acid addition salt is hydrochloride.

3. The process as defined in claim 1, in which the reaction is carried out in the presence of a solvent.

4. The process as defined in claim 3, in which the solvent is N,N-dimethylformamide, n-butanol, n-pentanol, n-hexanol, dimethylsulfoxide, ethylene glycol, 1,2-propylene glycol, or a mixture thereof.

5. The process as defined in claim 1, in which the reaction is carried out in the presence of a second base.

6. The process as defined in claim 5, in which the base is triethylamine, N,N-dimethylaniline, pyridine, or potassium acetate.

7. The process as defined in claim 1, in which the compound of formula (I) in the form of a (R)-(+)-isomer is prepared using (R)-(+)-1-methyl-1,2,3,4-tetrahydroisoquinoline.

8. The-process as defined in claim 1, in which the compound of formula (I) in the form of a (S)-(-)-isomer is prepared using (S)-(-)-1-methyl-1,2,3,4-tetrahydroisoquinoline.

* * * * *

UNITED STATES PATENT AND TRADEMARK OFFICE
CERTIFICATE OF CORRECTION

PATENT NO. : 5,990,311
DATED : November 23, 1999
INVENTOR(S) : You Wha HONG, Young Nam LEE It is certified that error appears in the above-identified patent and that said Letters Patent is hereby corrected as shown below:

ON THE TITLE PAGE, ITEM 73, "UHAN" SHOULD READ -- YUHAN --.

Signed and Sealed this

Twenty-seventh Day of June, 2000

Attest:

Q. TODD DICKINSON

*Attesting Officer*    *Director of Patents and Trademarks*